United States Patent [19]

Courvoisier et al.

[11] Patent Number: 4,513,197
[45] Date of Patent: Apr. 23, 1985

[54] HEATED SEAL OF RESILIENTLY COMPRESSIBLE FOAM FOR MATCHING THE EDGE OF A HOLLOW PORTION OF AN ARTICLE TO AN IRREGULAR SURFACE

[75] Inventors: Guy Courvoisier; Simon Arieh, both of Geneva, Switzerland

[73] Assignee: Battelle Memorial Institute, Carouge, Switzerland

[21] Appl. No.: 469,383

[22] Filed: Feb. 24, 1983

[30] Foreign Application Priority Data

Feb. 26, 1982 [CH] Switzerland .................... 1193/82

[51] Int. Cl.³ .................................... H05B 3/06
[52] U.S. Cl. .................... 219/527; 219/211; 219/535; 219/549; 128/380; 351/88
[58] Field of Search ............ 219/211, 212, 527, 528, 219/529, 535, 549; 428/304.4; 128/380, 399, 402; 351/88, 62; 338/210

[56] References Cited

U.S. PATENT DOCUMENTS

| | | | |
|---|---|---|---|
| 3,140,390 | 7/1964 | Smith et al. | 219/527 |
| 3,172,072 | 3/1965 | Willy | 338/210 |
| 3,238,355 | 3/1966 | Van Ecck | 219/528 |
| 3,657,515 | 4/1972 | Smith | 219/211 |
| 3,781,526 | 12/1973 | Damron | 219/528 X |
| 3,946,193 | 3/1976 | Giese | 219/211 |
| 4,035,606 | 7/1977 | Browder | 219/211 |

FOREIGN PATENT DOCUMENTS 0004829 10/1979 European Pat. Off. .

*Primary Examiner*—Volodymyr Y. Mayewsky
*Attorney, Agent, or Firm*—Karl F. Ross; Herbert Dubno

[57] ABSTRACT

An edge seal for articles such as goggles and earphones comprises two layers of foam of a thermo-formable material between which there is located a heating body whose ends terminate in terminals for connection to a current source so as to heat the foam to its thermo-forming temperature while e.g. the goggles are held tightly on the head of a user by an elastic strap. This enables the seal to be moulded to the shape of the user's face.

7 Claims, 2 Drawing Figures

HEATED SEAL OF RESILIENTLY COMPRESSIBLE FOAM FOR MATCHING THE EDGE OF A HOLLOW PORTION OF AN ARTICLE TO AN IRREGULAR SURFACE

FIELD OF THE INVENTION

The present invention relates to a seal of resiliently compressible foam, for matching the edge of a hollow portion of an article to an irregular surface, in the case of an article associated with means for holding the said edge and surface against one another. There are various devices of this sort such as protective goggles in general, in particular ski, motorcycle and sub-aqua goggles, and headphones for the telephone, radio and hi-fi systems, comprising a hollow portion with an edge which must be fitted to part of the head of a wearer.

BACKGROUND OF THE INVENTION

Because each person has a differently shaped head and these articles are mass produced and must fit everyone, the edge of the hollow portion is usually made of or provided with a resiliently deformable material, such as soft plastic or resiliently compressible plastic foam. In order to provide a suitable fit for the user the soft edge is pressed resiliently against the portion of the head which it is required to fit, so that the elastic deformation of this edge provides the best possible fit on the surface of the head against which it is applied, and forms a leak-tight seal to isolate the hollow portion from the surroundings, in order to shield the ears or eyes from the surrounding medium, either to protect them or to isolate them from external noise. The pressure exerted is a function of the size of the irregularities to be absorbed by the seal and the degree of compressibility of the material forming the seal. Consequently certain parts of the head are subjected to comparatively high local pressures which make wearing of the device uncomfortable or even painful after a certain time. In addition, the fit may not be very good, even with a non-negligible pressure, for example in the case of protective goggles for motorcycling or skiing where the seal frequently does fit properly on the base of the wings of the nose, leading to air infiltration which may cause ophthalmia.

Use has already been made of low density, nitrogen blown, polyethylene heat-formable foams in the medical field, in particular in order to mold this foam around various parts of the body in order to provide splints or orthopaedic supports or even to fit a prosthesis to an injured limb. The foam is heated to its softening temperature which is approximately 140° C. and is applied to the part of the body to which the foam is to be fitted, the foam being formed until it completely matches the desired shape.

A new application of this foam has been proposed, which consists in fitting an article of clothing to a part of the human body, as disclosed in European Patent Publication 0004829. In accordance with this publication, a plastics foam lining at least partly covers the internal face of a non-extensible casing and provides within this casing a receptacle whose dimensions are smaller than the corresponding dimensions of the part of the body to be fitted, so that the introduction of this part of the body into the cavity and the heating of the foam to its thermo-forming temperature enables the substantial stresses exerted on the part of the body to be eliminated and enables a cavity having dimensions which fit the part of the body to be provided. This technique is used to fit ski boots or helmets.

OBJECT OF THE INVENTION

It is the object of the present invention to remedy, at least in part, the drawbacks of the foam seals mentioned above by a new application of thermo-formable foams for the production of these seals.

SUMMARY OF THE INVENTION

The invention relates to a seal of resiliently compressible foam designed to fit the edge of a hollow portion of a device against an irregular surface, means being associated with this device to press the said edge and surface against one another, characterised in that the foam is of a thermo-formable material in which there is embedded a heating body extending over the entire periphery of the said edge and which has two ends that terminate in two connection terminals enabling the heating body to be conneted to an electrical current source.

BRIEF DESCRIPTION OF THE DRAWINGS

The accompanying drawing shows diagrammatically and by way of example, two embodiments of the seal of the invention.

SPECIFIC DESCRIPTION

Figure 1:
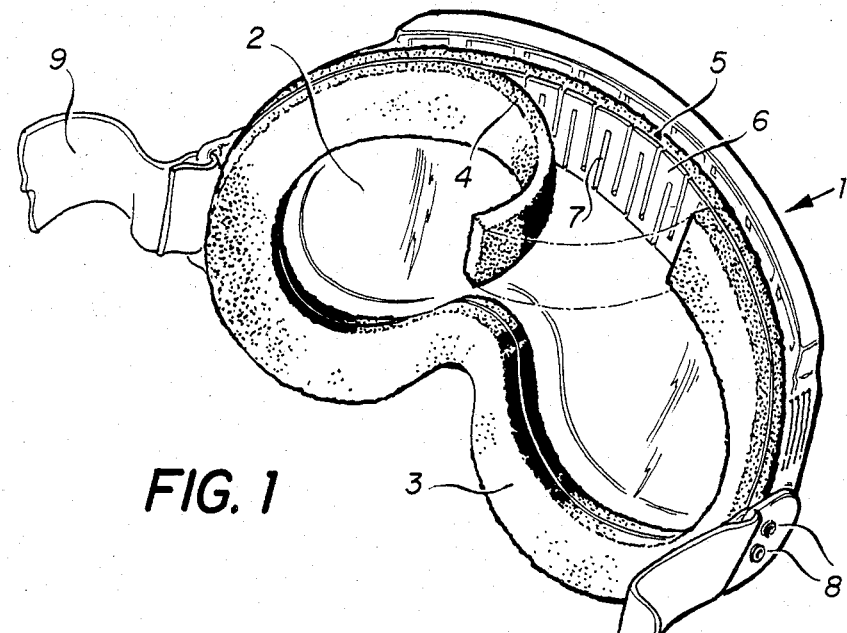
FIG. 1 is a perspective view of a first embodiment partly cut away, comprising a pair of goggles.

FIG. 1 shows protective goggles 1, for example ski or motorcycle goggles, comprising a cavity or recess formed by a transparent pane 2. The edge of the cavity is covered with a seal 3 constituted by two layers 4 and 5 of foam made from a thermo-formable material, such as low density polyethylene, between which there is disposed a heating body 6 consituted by an endless strip of aluminium having cut-out sections 7 starting alternately from the two opposite edges of the strip and each terminating short of the edge opposite to that from which it started thus forming a zigzag heating element. A similar result could be obtained using printed circuit techniques. The two ends of this heating body 6 terminate in two terminals 8 which enable the heating body to be connected to a low voltage electrical current source, for example 6 or 12 V. The goggles are provided with an elestic strap 9 enabling them to be fixed around the head.

When purchased, these goggles are similar to any goggles of this type, the shape of the seal 3 being produced in the factory in order to correspond roughly to the eye region of almost any individual, the elasticity of the foam of the seal 3 and the tightening of the elastic strap 9 enabling variations in face shapes to be more or less absorbed. In the case of the goggles of the invention, when the goggles have been fitted around the head of the future user, taking care to adequately tighten the elastic strap 9 so that the seal 3 provides the best possible fit for the face shape, the terminals 8 of the heating body 6 are connected to a low voltage current source (not shown) in order to bring the temperature of the foam to its softening temperature. In the case of the low density polyethylene foam, in this case a foam of 40 kg/m$_3$, the heat density is sufficiently low to prevent burning of the skin, even if the softening temperature is approximately 120° C. At this time the compression stresses in the foam lead to defomration which is permanent after cooling, such that the seal exactly fits the face surface of the intended user.

After this fitting operation has been carried out, the tension of the strap 9 when worn may be adjusted so that it only causes a very slight pressure of the seal 3 against the face. As the seal 3 has assumed, by means of thermo-forming, the shape of the face of the user, the strap is no longer required to hold the goggles tightly in order to produce an elastic deformation of the seal 3, but provides solely a pressure for holding the formed seal against the face. This leads not only to the elimination of local concentrations of pressure which may be uncomfortable, and even painful in the long term, but also means that the tension of the elastic strap 9 can be reduced to a minimum. Even with this reduced tension, local air leaks, in particular around the nose, are eliminated so that the user has goggles which are not painful, do not leave marks on the face and do not expose the eyes to droughts which may cause ophthalmia. It should also be noted that the foam of the seal can be moulded several times so that the same goggles can be fitted to several users.

Figure 2:
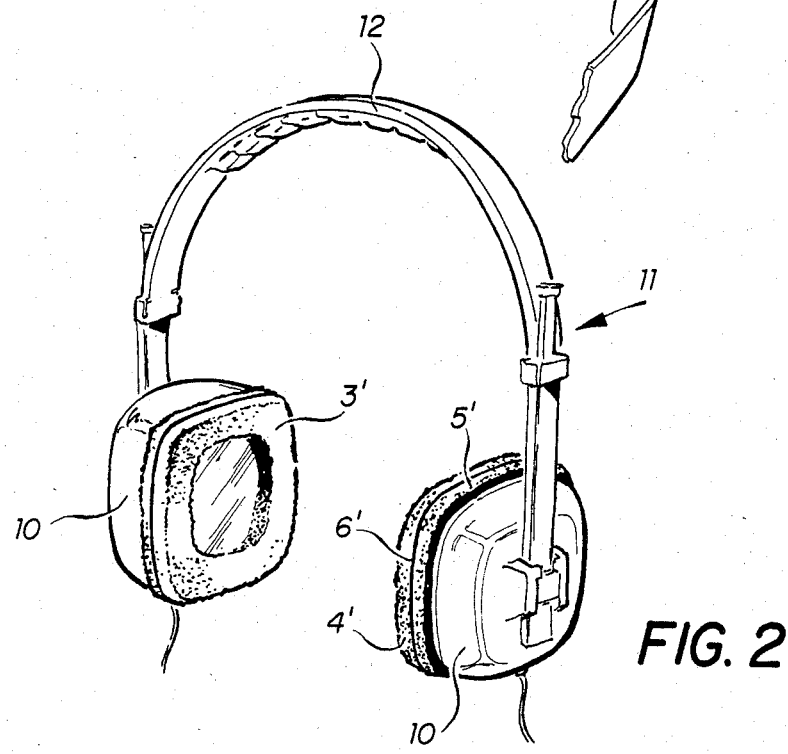
FIG. 2 is a perspective view of a second embodiment comprising a pair of headphones.

FIG. 2 shows an embodiment in which seal 3' of the invention is provided around the cavity of each ear piece 10 of headphones 11. In known headphones of this type the ear pieces 10 are connected to one another by a head-band 12 constituted by a leaf spring. As in the embodiment of FIG. 1, the seals 3' of the ear pieces 10 are formed from two layers 4' and 5' of a thermo-formable material between which there is interposed a heating body 6'. Fitting of the headphones 11 is carried out in the same way as for the goggles.

We claim:

1. An article adapted to be applied to a surface of the irregular contour and shape, comprising:

an object having at least an edge portion adapted to be turned toward said surface and sealingly fitted thereto;

a body of resiliently commmpressible thermally softenable foam material on said object at least in the region of said edge portion;

an electric heating body embedded in said body of foam material and substantially coextensive with a face thereof adapted to confront said surface; and electric terminals connected to said heating body for connection to a source of electric current to pass said electric current through said heating body to heat said body of foam material and thereby soften said body of foam material to cause the same to adopt the shape matching the shape and contour of said surface, thereby sealing said object to said surface at least all along said edge portion.

2. The article defined in claim 1 wherein said body has a cavity opening toward said surface and formed with said edge portion, said body of foam material being provided as a strip of foam material surrounding said cavity, said electric heating body being provided as a strip coextensive with the strip of foam material.

3. The article defined in claim 2, further comprising means on said object for pressing said edge portion against said surface.

4. The article defined in claim 3 wherein said means in a strap adapted to fit over the head of a user, said object being applicable to the head of a user.

5. The article defined in claim 4 wherein said object is a pair of goggles.

6. The article defined in claim 3 wherein said means includes a resilient support adapted to fit over the head of a user, said object including an earphone.

7. The article defined in claim 1 wherein said object includes an earphone.

* * * * *